(12) United States Patent
Shinzawa

(10) Patent No.: US 6,349,273 B1
(45) Date of Patent: Feb. 19, 2002

(54) ATOMIC COORDINATES GENERATING METHOD

(75) Inventor: Tsutomu Shinzawa, Tokyo (JP)

(73) Assignee: NEC Corporation, Tokyo (JP)

( * ) Notice: Subject to any disclaimer, the term of this patent is extended or adjusted under 35 U.S.C. 154(b) by 0 days.

(21) Appl. No.: 09/241,068

(22) Filed: Feb. 1, 1999

(30) Foreign Application Priority Data

Feb. 2, 1998  (JP) ............................................. 10-020611

(51) Int. Cl.[7] ............................ G06G 7/48; G21K 7/00; G01N 23/207
(52) U.S. Cl. ................................. 703/6; 378/43; 378/73
(58) Field of Search ................. 703/6; 378/43, 378/73

(56) References Cited

U.S. PATENT DOCUMENTS

| | | | | |
|---|---|---|---|---|
| 3,816,747 A | * | 6/1974 | Kishino ........................ 378/73 |
| 4,247,771 A | * | 1/1981 | Frevel ........................... 378/75 |
| 4,426,719 A | * | 1/1984 | Fraenkel ........................ 378/70 |
| 4,788,702 A | * | 11/1988 | Howe et al. ................... 378/73 |
| 5,245,648 A | * | 9/1993 | Kinney et al. ................. 378/43 |
| 5,353,236 A | * | 10/1994 | Subbiah ........................ 700/266 |
| 5,365,456 A | * | 11/1994 | Subbiah ........................ 703/5 |
| 5,371,778 A | * | 12/1994 | Yanof et al. ................... 378/4 |
| 5,455,952 A | * | 10/1995 | Gjovaag ........................ 717/1 |
| 5,517,602 A | * | 5/1996 | Natarajan .................... 345/419 |
| 5,568,384 A | * | 10/1996 | Robb et al. .................. 707/532 |
| 5,594,842 A | * | 1/1997 | Kaufman et al. ............ 345/424 |
| 5,631,974 A | * | 5/1997 | Lau-Kee et al. ............. 382/132 |
| 5,672,877 A | * | 9/1997 | Liebig et al. ........... 250/363.04 |
| 5,748,509 A | * | 5/1998 | Fewster ........................ 703/6 |
| 5,787,889 A | * | 8/1998 | Edwards et al. ............. 600/443 |
| 5,916,163 A | * | 6/1999 | Panescu et al. .............. 600/424 |
| 5,937,083 A | * | 8/1999 | Ostuni ......................... 382/131 |
| 5,970,499 A | * | 10/1999 | Smith et al. ................. 707/104 |
| 5,982,378 A | * | 11/1999 | Kato ............................ 345/430 |
| 5,986,662 A | * | 11/1999 | Argiro et al. ................ 345/424 |
| 5,999,840 A | * | 12/1999 | Grimson et al. ............ 600/424 |
| 6,006,126 A | * | 12/1999 | Cosman ...................... 600/426 |
| 6,016,439 A | * | 1/2000 | Acker .......................... 600/411 |
| 6,049,622 A | * | 4/2000 | Robb et al. .................. 382/128 |
| 6,051,834 A | * | 4/2000 | Kakibayashi et al. ....... 250/311 |
| 6,052,476 A | * | 4/2000 | Qian et al. ................... 382/130 |
| 6,071,288 A | * | 6/2000 | Carol et al. .................. 606/130 |
| 6,175,655 B1 | * | 1/2001 | George et al. ............... 382/257 |

OTHER PUBLICATIONS

Johnson et al.; "A computational steering model applied to problems in medicine"; IEEE Proc. Supercomputing '94; pp. 540–549; Nov. 1994.*

(List continued on next page.)

*Primary Examiner*—Kevin J. Teska
*Assistant Examiner*—Hugh Jones
(74) *Attorney, Agent, or Firm*—Sughrue Mion, PLLC

(57) ABSTRACT

An atomic coordinates generating method generating an atomic coordinate position within a rectangular parallelepiped as an outer frame of a crystal having a predetermined plane orientation derives a sphere circumscribing the rectangular parallelepiped, derives a cubic circumscribing the sphere, generates atomic coordinates within the cubic, provides rotation for the generated atomic coordinates for matching a bottom of the cubic with the plane orientation, checks whether the atomic coordinates after rotation are present within a rectangular parallelepiped having the predetermined plane orientation, and selects only coordinates present within the rectangular parallelepiped.

13 Claims, 4 Drawing Sheets

OTHER PUBLICATIONS

Bardaczek; "Automated X–ray sorting machine for round quartz blanks"; IEEE Proc. 45th Symp. Frequency Control; pp. 114–116; May 1991.*

Morys et al.; "Improved Omega–scan for separate measurement of true AT–cutting angles and X–miscutting angles for round quartz blanks"; Proc. 48th Int. Frequency Control; pp. 237–240; Jun. 1994..*

Kalashinkova et al.; "Gamma–ray diffractometry method for nondestructive dislocation density control in massive quartz crystals"; Proc. 50th Frequency Control Symp.; pp. 109–112; Jun. 1996.*

Nelson et al.; "Visualization of 3D ultrasound data"; IEEE Comp. Graphics and Appl.; pp. 50–57; Nov. 1993.*

Tsalpatouros et al.; "CT–based software for 3–D localization and reconstruction in stepping source brachtherapy"; IEEE Trans. Info. Tech. in Biomedicine; pp. 229–242; Dec. 1997.*

Parker et al.; "An integrated problem solving environment: the SCIRun computational steering system"; Proc. Hawaii Int. Conf. Systems Sciences (IEEE); pp. 147–156; Jan. 1998.*

M.J. Weins, "Structure and Energy of Grain Boundaries", Surface Science, vol. 31, (1972), pp. 138–160.

* cited by examiner

ATOMIC COORDINATES GENERATING METHOD

BACKGROUND OF THE INVENTION

1. Field of the Invention

The present invention relates to a method for generating atomic coordinates required upon performing material simulation.

2. Description of the Related Art

For performing material simulation by molecular dynamics, molecular orbital methods and so forth, an initial arrangement of all objective crystal atoms is necessary. A crystal model is defined by designating all coordinates of the atoms that are included in the crystal. Particularly, when the crystal includes a grain boundary, it is required to arrange each crystal grain with tilting at a certain angle to form a desired grain boundary. Conventionally, an atomic coordinate generating method of this kind has been disclosed in Surface Science, Vol. 31, (1972), pp. 138 to 160. Necessary crystal grains are prepared per surface orientations and are rotated around the surface normal to form a symmetric grain boundary that is a mirror surface to prepare a replica of atom at a reversed image position.

In the prior art set forth above, generation methods of atom positions per surface orientation must be prepared. Therefore, surface orientation generating means have to be prepared for required surface orientations. Also, since the prepared means are differentiated per surface orientation, the program becomes complicated. Furthermore, since the rotated crystal must be cut off to make a basic cell, an extra temporary storage region is required.

SUMMARY OF THE INVENTION

A first object of the present invention is to prepare a method and a system for generating atomic coordinates which can easily and efficiently perform generation of coordinate data of model atoms forming a crystal body having a designated surface orientation.

A second object of the present invention is to provide a method and a system for generating atomic coordinates to avoid formation of any "defect" in the prepared crystal model.

A third object of the present invention is to provide a method and a system for generating atomic coordinates which can restrict a storage region to be used in a small range.

According to the first aspect of the invention, an atomic coordinates generating method that generates atomic coordinate positions within a rectangular parallelepiped as an outer frame of a crystal having a predetermined plane orientation is provided, comprising:

(1) step of deriving a sphere circumscribing said rectangular parallelepiped, (2) step of deriving a cubic circumscribing said sphere, (3) step of generating atomic coordinates within said cubic, (4) step of providing rotation for the generated atomic coordinates for matching a bottom of said cubic with said plane orientation, and (5) step of checking whether the atomic coordinates after rotation is present within a rectangular parallelepiped having said predetermined plane orientation, and selecting only coordinates present within said rectangular parallelepiped.

In the preferred construction, said atomic coordinates generating step comprises (a) step of deriving a repetition number of a unit crystal in each crystal axis direction, and (b) step of generating the atomic position coordinates on the basis of said repetition number and an atom position within a unit cell.

In another preferred construction, said atomic coordinates generating step comprises (a) step of deriving a repetition number of a unit cell in each crystal axis direction, and (b) step of generating the atomic position coordinates on the basis of said repetition number and atom positions within a unit cell, steps from (b) to (5) are repeated for all atomic coordinates within said cubic.

In another preferred construction, respective edges of said cubic are parallel to x, y and z axes of orthogonal coordinates and (001) plane of crystal included in said rectangular parallelepiped is parallel to an x-y plane of said orthogonal coordinates.

In another preferred construction, respective edges of said cubic are parallel to x, y and z axes of orthogonal coordinates and (001) plane of crystal included in said rectangular parallelepiped is parallel to an x-y plane of said orthogonal coordinates, in advance of said step (4), a rotational transformation matrix being obtained beforehand for placing said plane orientation in parallel with said x-y plane.

According to the second aspect of the invention, an atomic coordinates generating system generating an atomic coordinate position within a rectangular parallelepiped as an outer frame of a crystal having a predetermined plane orientation, comprises means for inputting a crystal size, a lattice constant, relative atom positions in the unit cell and a Miller indices as parameters, position generating means, and region calculating means for deriving a sphere circumscribing said rectangular parallelepiped from said crystal size, deriving a size of a cubic circumscribing said sphere, and deriving repetition number of unit cell on the basis of the size of said cubic and said lattice constant, as a position generating region, atomic position generating means for generating the unit cell within said position generating region and generating atom coordinates according to said relative atom positions in the unit cell, rotational transformation means for providing rotation for matching a bottom of said cubic with said plane orientation with respect to derived atomic coordinates, and region judgment means for checking whether the atom coordinates after rotation are present within the rectangular parallelepiped having said predetermined plane orientation and selecting only atom coordinates presenting within said rectangular parallelepiped.

In the preferred construction, respective edges of said cubic are parallel to x, y and z axes of orthogonal coordinates and (001) plane of crystal included in said rectangular parallelepiped is parallel to an x-y plane of said orthogonal coordinates, said system further comprises means for obtaining beforehand a rotational transformation matrix for placing said plane orientation in parallel with said x-y plane in advance of process by said rotational transformation means.

In another preferred construction, a process of generation of atomic coordinates by said atomic position generating means to selection by said region judgment means is repeated for all atomic coordinates within said cubic.

According to another aspect of the invention, a computer readable memory storing atomic coordinates generating program generating atomic coordinate positions within a rectangular parallelepiped as an outer frame of having a predetermined plane orientation, as loaded and executed by a computer, said atomic coordinates generating program comprises (1) step of deriving a sphere circumscribing said rectangular parallelepiped, (2) step of deriving a cubic circumscribing said sphere, (3)

step of generating atomic coordinates within said cubic, (4) step of providing rotation for the generated atomic coordinates for matching a bottom of said cubic with said plane orientation, and (5) step of checking whether the atomic coordinates after rotation are present within a rectangular parallelepiped having said predetermined plane orientation, and selecting only coordinates present within said rectangular parallelepiped.

Further objects, features and effects of the present invention will become apparent from the detailed description given hereinafter.

BRIEF DESCRIPTION OF THE DRAWINGS

The present invention will be understood more fully from the detailed description given hereinafter and from the accompanying drawings of the preferred embodiment of the present invention, which, however, should not be taken to be limitative to the invention, but are for explanation and understanding only.

In the drawings.

DESCRIPTION OF THE PREFERRED EMBODIMENT

Figure 1:
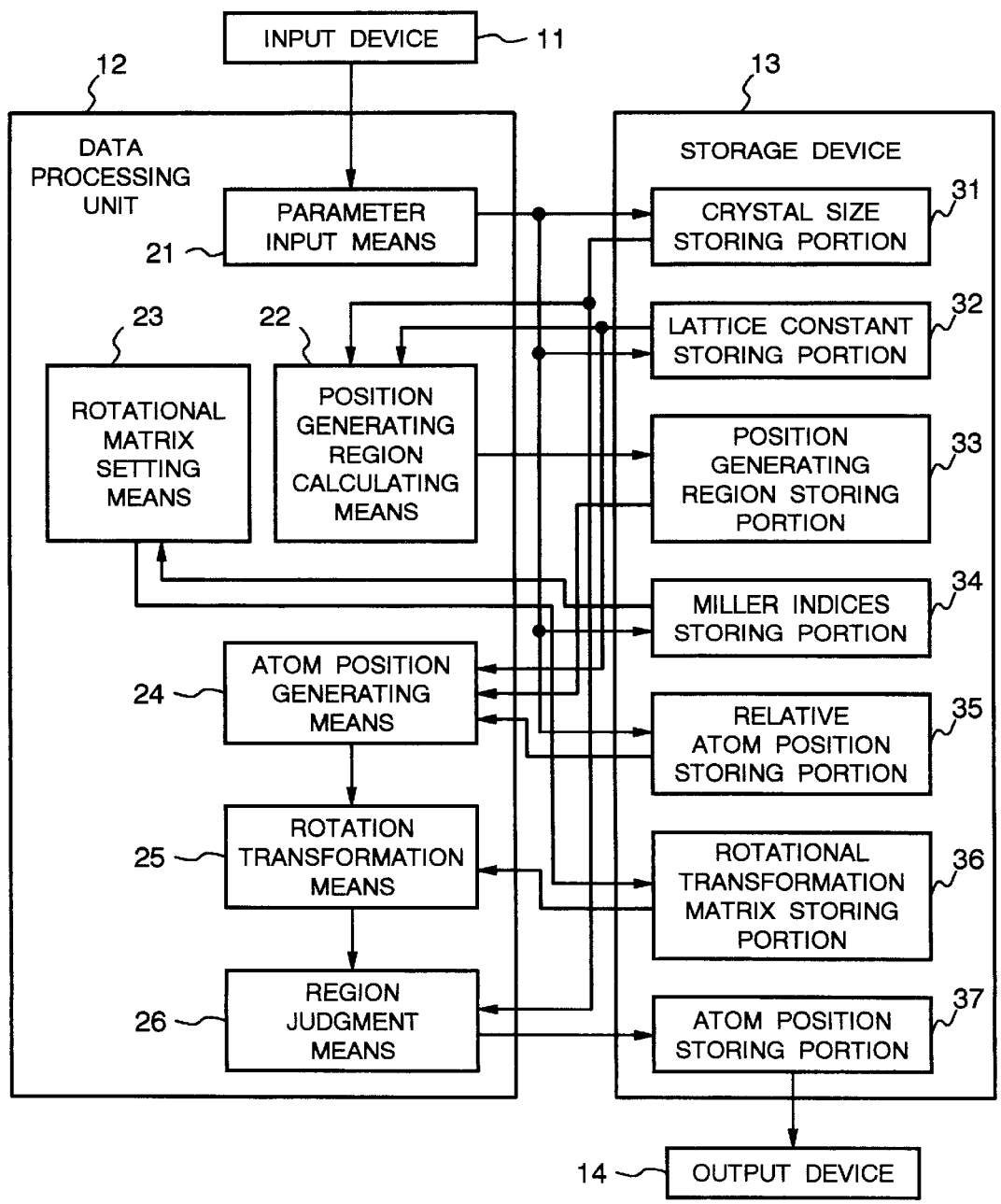
FIG. 1 is a block diagram of a processing system for explaining the preferred embodiment of atomic coordinate generating method and system according to the present invention.

The present invention will be discussed hereinafter in detail in terms of the preferred embodiment of the present invention with reference to the accompanying drawings. In the following description, numerous specific details are set forth in order to provide a thorough understanding of the present invention. It will be obvious, however, to those skilled in the art that the present invention may be practiced without these specific details. In other instance, well-known structures are not shown in detail in order to avoid unnecessarily obscure the present invention.

An atomic position generating method according to the present invention has a crystal size, lattice constant, relative atom positions in a unit cell and a Miller indices as input data, derives a radius of a sphere circumscribing a rectangular parallelepiped including a crystal, and then derives a length of one edge of a cubic circumscribing the sphere. Repetition number of a unit cell is derived on the basis of obtained length of one edge of the cubic and the unit cell lengths. A rotational transformation matrix providing rotation, in which a surface designated by the Miller indices becomes parallel to an x-y plane is obtained beforehand and stored.

According to repetition number in each axis direction, a unit cell is prepared, and atom positions are generated according to relative atom positions in the unit cell. After rotating the atom position on the basis of the stored rotational transformation matrix, check is performed whether the atom position after the rotation is included in the crystal size as the input data, and then the atom position is taken for registration only when the atom position falls within the crystal size.

By the atomic coordinate generating method according to the present invention, the rotational transformation matrix for providing rotation to place the surface designated by the Miller indices provided as the input data in parallel to the x-y plane, is obtained and stored. Then, the atom position is generated in a cubic circumscribing the rectangular parallelepiped including the objective crystal at any angular position as rotated about the center point, and rotation is provided for the atom position by preliminarily stored rotational transformation matrix. Therefore, by preparing the atom position at only one orientation, the atom position in all orientation can be easily generated. Repetition numbers in each axes of the unit cell in the cubic and relative atom positions in the unit cell are stored, and only atoms positioned in the rectangular parallelepiped having provided surface orientation are stored. Therefore, the necessary storage region can be restricted in a small range. Namely, according to the present invention, the program can be simplified to provide general applicability. Also, extra storage capacity for storing the atom position registration can be avoided. Since the atom position is generated within the cubic that can circumscribe the objective crystal at any rotational position, a crystal model having no "defect" can be prepared.

FIG. 1 is a block diagram for explaining the preferred embodiment of the atomic coordinate generating method and the system according to the present invention. The atomic coordinate generating system for realizing the atomic coordinate generating method according to the present invention is constructed with an input device 11, such as a keyboard or the like, a data processing unit 12 operating under program control, a storage device 13 storing information and an output device, such as a display device, a printing device and so forth.

The storage device 13 has a crystal size storing portion 31, lattice constant storing portion 32, a position generating region storing portion 33, a Miller indices storing portion 34, a relative atom position storing portion 35, a rotational transformation matrix storing portion 36 and an atom position storing portion 37.

The data processing unit 12 has parameter input means 21, position generating region calculating means 22, rotational matrix setting means 23, atom position generating means 24, rotational transformation means 25 and region judgment means 28.

The parameter input means stores the crystal size, lattice constant, the relative atom position in the unit cell and Miller indices at respectively corresponding storing portions.

The position generation region calculating means 22 makes reference to values from the crystal size storing portion 31 and the lattice constant storing portion 32 to derive a radius R of a sphere circumscribing to the rectangular parallelepiped including the crystal, and to derive a crystal size of the cubic including the sphere. Then, the position generating region calculating means 22 derives repetition number of unit cell included in the crystal per axis a, b and c to store in the position generating region storing portion 33.

The rotational matrix setting means 23 calculates the rotational transformation matrix for placing the predetermined surface designated by the Miller indices in parallel to the x-y plane.

The atom position generating means 24 generates a lattice within the position generating region stored in the position generating region storing portion 33 so that (001) plane of the crystal is placed in parallel to the x-y plane, and a-axis of the crystal, namely [100] vector is oriented to be parallel to the x-axis, and generates the atom position according to the parameter of the relative atom positions in the unit cell stored in the relative atom position storing portion 35.

The rotation transformation means 25 rotates the atom position generated by the atom position generating means 24 according to the rotational transformation matrix set by the rotational matrix setting means 23.

The region judgment means 26 checks whether the atom position rotated by the rotational transformation means 25 falls within the crystal size stored in the crystal size storing portion 31 or not so that the atom position is stored in the atom position storing portion 37 only when the atom position falls within the crystal size.

Next, atomic coordinates generating operation in the preferred embodiment of the atomic coordinates generating method according to the present invention will be discussed with reference to FIGS. 1 and 2.

Figure 2:
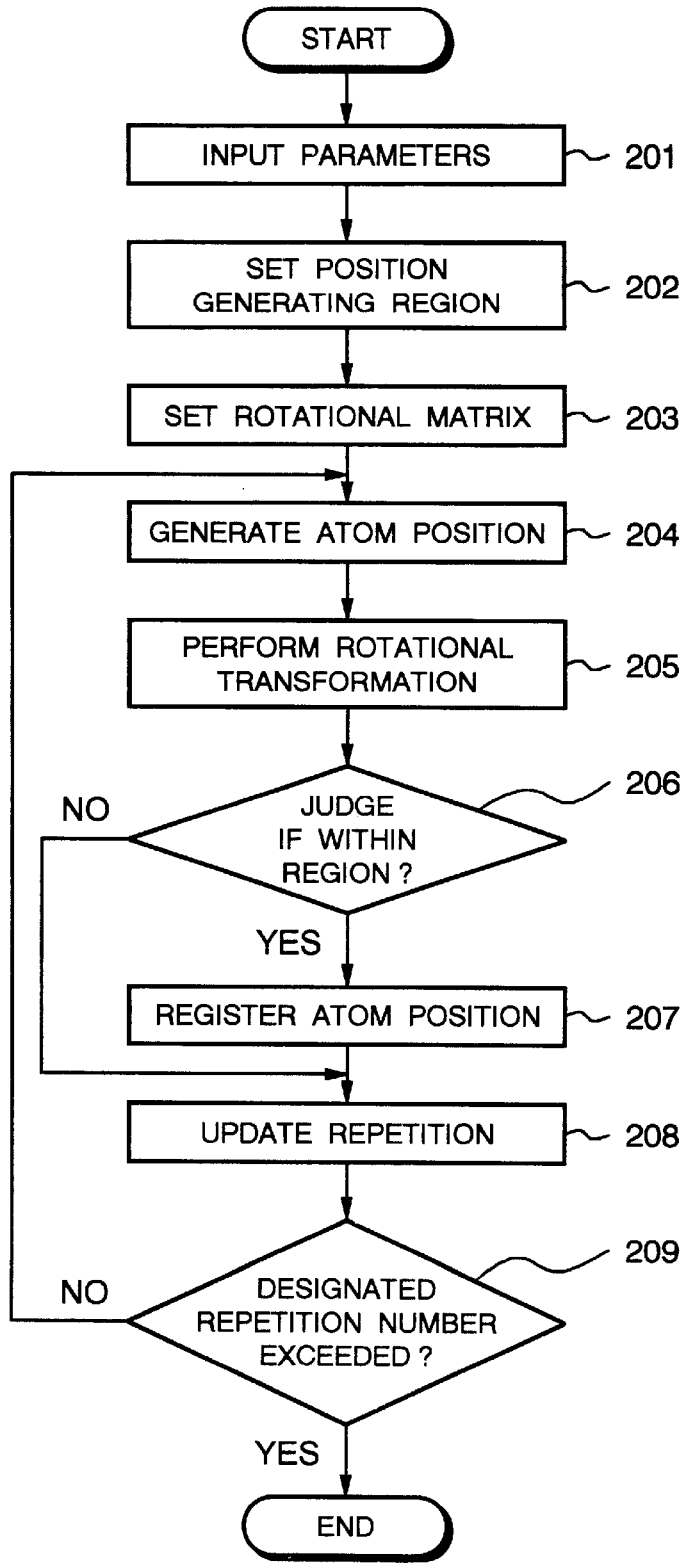
FIG. 2 is a flowchart for explaining the preferred embodiment of the atomic coordinate generating method and system according to the present invention.

FIG. 2 is a flowchart showing operation of atomic coordinate generation in accordance with the present invention. Parameters input through the input device 11 is discriminated by the parameter input means 21 and respectively stored in respective storing portions, namely in the crystal size storing portion 31, the lattice constant storing portion 32, the relative atom position storing portion 35 and the Miller indices storing portion 34 as the crystal size, the lattice constant, the relative atom position and the Miller indices (step 201).

The position generating region setting means 22 derives the radius R of the sphere circumscribing the crystal on the basis of the crystal size by using the crystal size and the lattice constant stored in the crystal size storing portion 31 and the lattice constant storing portion 32, calculates the crystal size of cubic including the sphere, derives repetition number of the unit cell included in the crystal on the basis of the lattice constant and the calculated cubic size per each axis a, b and c to store in the position generating region storing portion 33 as the position generating region (step 202).

At first, the radius R of the sphere circumscribing the crystal is expressed by:

$$R = \sqrt{(L_x^2 + L_y^2 + L_z^2)}/2 \quad (1)$$

wherein $L_x$, $L_y$ and $L_z$ represent lengths of each edge of the rectangular parallelepiped indicative of size of the crystal.

Figure 3:
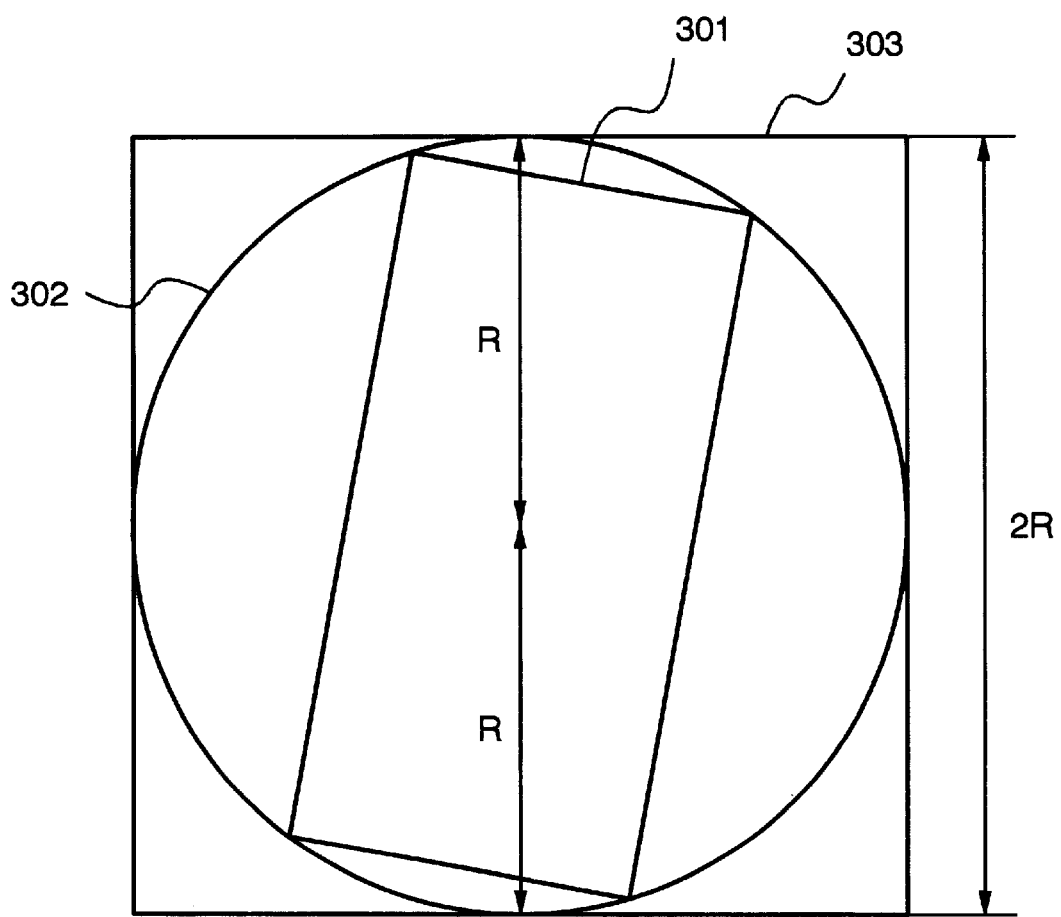
FIG. 3 is an illustration showing an arrangement relationship of a crystal for explaining the preferred embodiment of the atomic coordinate generating method and system according to the present invention.

So that the rectangular parallelepiped of the crystal may be included in the sphere, the center of the rectangular parallelepiped is made common to the center of the sphere. Considering the cubic circumscribing the sphere, a length of one edge is 2R as shown in FIG. 3. The atom position is generated within this cubic. Since this cubic includes the sphere and the sphere includes the rectangular parallelepiped holding the necessary crystal size, the inside of the rectangular parallelepiped can be inherently filled by generating the atom position within the cubic. This relationship may prevent the rectangular parallelepiped to be extended from the sphere at any rotational angular position relative to the axis extending through the center, as shown in FIG. 3.

Next, from thus obtained length 2R of the one edge of the obtained cubic and the lattice constant read out from the lattice constant storing portion 32, the repetition number of the unit cell is derived. The lattice constants a, b, and c are length of the unit cell along respective axes to set those as a, b and c (here, assuming symmetry of the oblique crystal system, and axial angle is assumed to be 90 degrees). The repetition number $I_x$, $I_y$, and $I_z$ of the unit cell included within the cubic having radius 2R. $I_x$, $I_y$, and $I_z$ are expressed by the following equations:

$$I_x = [2R/a] + 1 \quad (2)$$

$$I_y = [2R/b] + 1 \quad (3)$$

$$I_z = [2R/c] + 1 \quad (4)$$

wherein [x] is a sign of gauss and is a function returning a maximum integer not exceeding a real number x.

The repetition number $I_X$ $I_Y$ and $I_Z$ of the unit cell derived as set forth above are stored in the position generating region storing portion 33.

Among parameters, by the Miller index, a required plane is designated. The Miller index is defined as most simple integer ratios h, k, l of 1/p, 1/q and 1/r assuming that intersections of the designated plane and the crystal axes are p, q and r (wherein, 0 in case of not intersecting).

Here, the atom position is generated so that the x-y plane and (001) plane are parallel. Namely, the (001) plane is take as reference. Then, rotation where (hkl) plane becomes parallel to the x-y plane is considered. For this purpose, deriving a vector perpendicular to the (hkl) plane, and rotating so that the vector coincides with z-axis, (hkl) plane becomes parallel to the x-y plane. The reason is that the z-axis and the x-y plane are perpendicular to each other.

Figure 4:
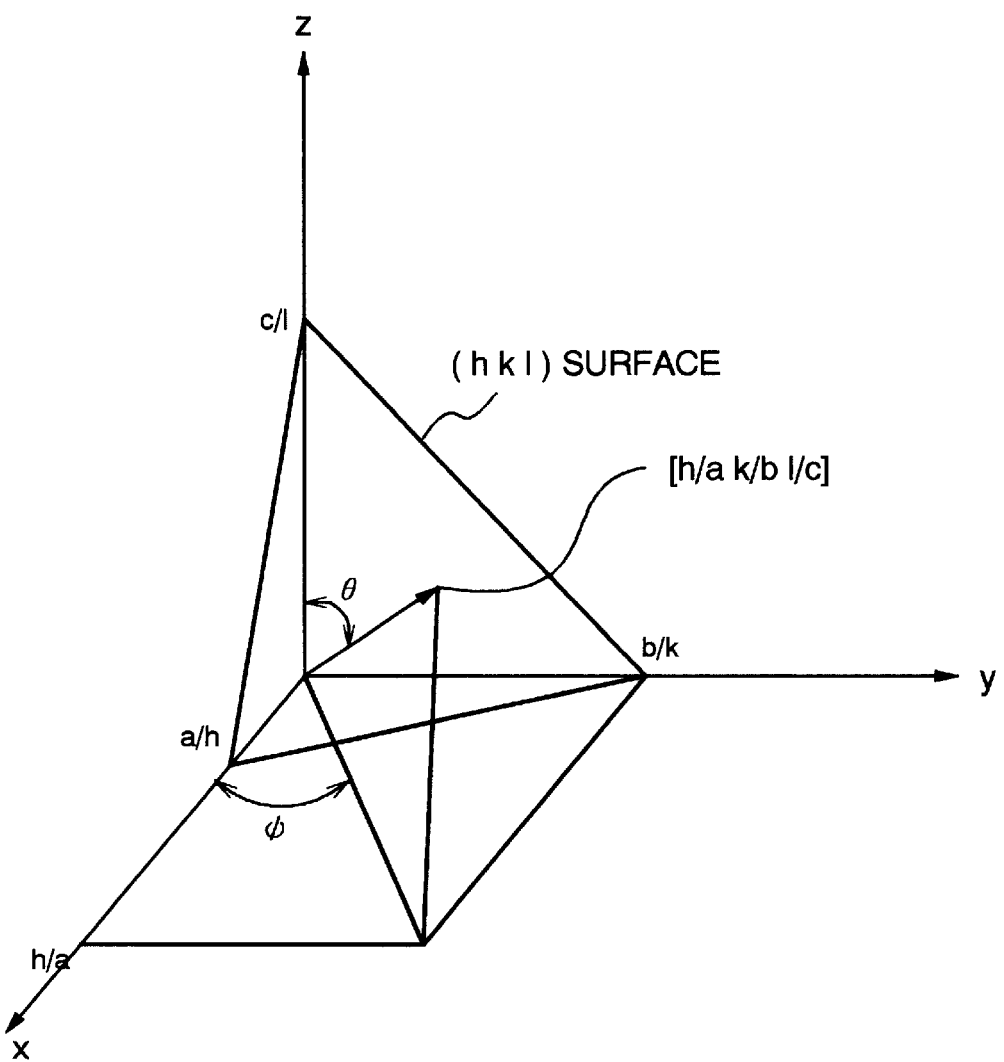
FIG. 4 is an illustration showing rotation of a surface designated by a Miller indices for explaining the preferred embodiment of the atomic coordinate generating method and system according to the present invention.

Next, manner for deriving the vector perpendicular to the (hkl) plane will be discussed. FIG. 4 shows a relationship between the (hkl) plane identified by the Miller indices (hkl) and a vector perpendicular to the (hkl) plane. As shown in FIG. 4, the (hkl) plane intersects with respective of x, y and z axes at respective points (a/h, 0, 0), (0, b/k, 0) and (0, 0, c/l) as being defined in the Miller indices. An equation of this plane is expressed as following equation, assuming that x, y and z components of the vector perpendicular to the (hkl) plane are respectively [pqr] and that an arbitrary point (x0, y0, z0) is in this plane:

$$p(x-x0) + q(y-y0) + r(z-z0) = 0$$

Replacing with the foregoing three intersecting points with respective axes, a ratio of p, q and r can be expressed as:

$$p:q:r = (h/a):(k/b):(l/c)$$

Therefore, the vector perpendicular to the (hkl) plane can be identified by [h/a, k/b, l/c].

As shown in FIG. 4, $\psi$ is assumed as an angle formed by a plane including the z-axis and the vector [h/a, k/b, l/c] and xy plane, and $\theta$ is an angle formed by z-axis and the vector [h/a, k/b, l/c]. $\psi$ and $\theta$ can be derived by the following equations (5) and (6)

$$\psi = \cos^{-1}\left(\frac{h}{a\sqrt{\left(\frac{h}{a}\right)^2 + \left(\frac{k}{b}\right)^2}}\right) \quad (5)$$

$$\theta = \cos^{-1}\left(\frac{l}{c\sqrt{\left(\frac{h}{a}\right)^2 + \left(\frac{k}{b}\right)^2 + \left(\frac{l}{c}\right)^2}}\right) \quad (6)$$

Among rotation to place the vector perpendicular to the (hkl) plane consistent with z-axis, rotation for $-\theta$ about y-axis after rotation for $-\psi$ about z-axis is selected. A rotational matrix expressing the rotation matrix and composite rotation are as follows:

rotation for $-\psi$ about z-axis is expressed by:

$$\begin{pmatrix} \cos\psi & \sin\psi & 0 \\ -\sin\psi & \cos\psi & 0 \\ 0 & 0 & 1 \end{pmatrix} \quad (7)$$

rotation for $-\theta$ about y-axis is expressed by:

$$\begin{pmatrix} \cos\theta & 0 & -\sin\theta \\ 0 & 1 & 0 \\ \sin\theta & 0 & \cos\theta \end{pmatrix} \quad (8)$$

Accordingly, the composite rotation is expressed by:

$$\begin{pmatrix} \cos\theta & 0 & -\sin\theta \\ 0 & 1 & 0 \\ \sin\theta & 0 & \cos\theta \end{pmatrix} \begin{pmatrix} \cos\psi & \sin\psi & 0 \\ -\sin\psi & \cos\psi & 0 \\ 0 & 0 & 1 \end{pmatrix} \quad (9)$$

Namely, the following equation (10) is established.

$$\begin{pmatrix} \cos\theta\cos\psi & \cos\theta\sin\psi & -\sin\theta \\ -\sin\psi & \cos\psi & 0 \\ \sin\theta\cos\psi & \sin\theta\sin\psi & \cos\theta \end{pmatrix} \quad (10)$$

Each components of the matrix is calculated using $\psi$, $\theta$ derived through the foregoing equations (5) and (6) from the Miller indices (hkl) and the foregoing equation (10), and stored in the rotational transformation matrix storing portion 36 (step 203).

Next, unit cells are prepared according to repetition number in respective axis directions stored in the position generating region storing portion 33 by the atom position generating means 24 to generate the atom position according to the relative atom positions in the unit cell held in the relative atom position storing portion 35 (step 204).

Next, using the rotational transformation matrix held in the rotational transformation matrix storing portion 36, rotational transformation of the atom position generated at step 204 is performed by the rotational transformation means 25 (step 205).

Next, check is performed whether the coordinates transformed at step 205 is included within the crystal size held in the crystal size storing portion 31 (step 206). Only when the coordinates transformed at step 205 is included within the crystal size, the position is stored in the atom position storing portion 37 and output using the output device 14 (step 207). Next, updating of the repetition number is performed (step 208). Then, check is performed whether the repetition number exceeds a designated number or not (step 209). If not exceeded, the process is returned to step 204, and if exceeded, process goes end.

Next, particular example of the present invention will be discussed in detail. The following table 1 shows contents of the input data relating to one particular embodiment of the present invention.

TABLE 1

| | | | |
|---|---|---|---|
| Lattice Constant (Å) | 4.05 | 4.05 | 4.05 |
| Relative atom coordinates in the unit cell | 0.0 | 0.0 | 0.0 |
| | 0.5 | 0.0 | 0.5 |
| | 0.0 | 0.5 | 0.5 |
| | 0.5 | 0.5 | 0.0 |
| Crystal Size (Å) | 15.0 | 15.0 | 15.0 |
| Miller indices | 1 | 1 | 1 |

The first row in the foregoing table shows the lattice constant of a face centered cubic crystal consisted of aluminum atom. The second to fifth rows show positions of atom within the unit cell expressed as a ratio relative to respective components of the lattice constant. The sixth row represents required crystal size and seventh row represents the Miller indices designating the required plane.

These parameters are read from the input device 11 and are stored in the lattice constant storing portion 32, the relative atom position storing portion 35, the crystal size storing portion 31 and the Miller indices storing portion 34 by the parameter input means 21.

Next, by the position generating region calculating means 22, the repetition number of the unit cell is calculated. In this case, the radius of the sphere circumscribing the crystal is $\sqrt{675}/2$. A length of one edge of the cubic circumscribing the sphere is $\sqrt{675}$. The repetition number $I_X$, $I_Y$, $I_Z$ of the unit cell are all "7" from the foregoing equations (2) to (4). Accordingly, with 7×7×7 of unit cells, the cubic 303 circumscribing the foregoing sphere 302 can be filled.

Next, rotational transformation matrix is calculated by the rotation matrix setting means 23. In this case, $$\psi = \cos^{-1}(1/\sqrt{2})$$
$$= 45°$$
$$\theta = \cos^{-1}(1/\sqrt{3})$$
$$= 54.73°$$

Replacing the equation (10) with these, the following equation (11) is established.

$$\begin{pmatrix} \frac{\sqrt{6}}{6} & \frac{\sqrt{6}}{6} & -\frac{\sqrt{6}}{3} \\ -\frac{\sqrt{2}}{2} & \frac{\sqrt{2}}{2} & 0 \\ \frac{\sqrt{3}}{3} & \frac{\sqrt{3}}{3} & \frac{\sqrt{3}}{3} \end{pmatrix} \quad (11)$$

Next, reference is made to the repetition number $I_X$, $I_Y$, $I_Z$ in each axis direction held in the position generating region storing portion 33 to generate the position of the origin of the unit cell by the atom position generating means 24 for offsetting the atom position. A value derived by multiplying the relative atom position in the unit cell held in the relative atom position storing portion 35 by the lattice constant in each axis direction is generated per atom within the unit cell for number of the atoms within the unit cell to add in the unit cell position as follow.

$$(x, y, z) = (a(i+Pa), b(j+Pb), c(k+Pc))$$

wherein Pa, Pb and Pc show atom positions within the unit cell, (i, j, k) is indicia indicative of the position of the unit cell.

Next, using the equation (11) of the rotational transformation matrix held in the rotational transformation matrix storing portion 36, rotational transformation of the atom position generated at step 204 by the rotational transformation means 25 is performed to obtain new coordinates (X, Y, Z) expressed by the following equations (12) to (14) (step 20)

$$X = \frac{\left(\frac{x\sqrt{2}}{2} + \frac{y\sqrt{2}}{2}\right)\sqrt{3}}{3} - \frac{z\sqrt{6}}{3} \quad (12)$$

$$Y = \frac{y\sqrt{2}}{2} - \frac{x\sqrt{2}}{2} \quad (13)$$

$$Z = \frac{\left(\frac{x\sqrt{2}}{2} + \frac{y\sqrt{2}}{2}\right)\sqrt{6}}{3} + \frac{z\sqrt{3}}{3} \quad (14)$$

Next, check is performed whether the coordinates (X, Y, Z) transformed at step 205 is included within the crystal size (15, 15, 15) held in the crystal size storing portion 31 using the region judgment means 26 (step 206). If the transformed coordinates are included within the crystal, the coordinates are stored in the atom position storing portion 37, and in conjunction therewith, output by the output device 14 (step 207).

Next, updating of repetition number is performed (step 208). Then, when the repetition number does not exceed the designated number, the process is returned to step 204. On the other hand, if exceeded, the process goes end.

The foregoing atomic coordinates generating system of the preferred embodiment of the present invention is realized by a program controlled CPU and RAM or other internal memory in a work station, personal computer or other computer system. The atomic coordinate generating program realizing the foregoing function has been provided in a form stored in a typical storage medium, such as a magnetic disk, an optical disk, a semiconductor memory and so forth, and is loaded in the internal memory of the computer system to control CPU to realize function of respective components.

As set forth above, the present invention derives the cubic having a plane parallel to the x-y plane circumscribing sphere circumscribing the rectangular parallelepiped having given plane orientation. Then, the atom position within the cubic is generated and atomic coordinates of the desired crystal are generated by rotating in a magnitude corresponding to plane orientation. Thus, the following effect can be achieved.

1) The atom position of the crystal model having the plane in arbitrary orientation can be easily generated.
2) Occurrence of "defect" in the generated crystal model can be successfully prevented.
3) By storing the repetition number of the unit crystal within a minimum cubic in the position generating region storing portion and only atom position within the desired crystal is stored, the storage region to be used can be made small range.

Although the present invention has been illustrated and described with respect to exemplary embodiment thereof, it should be understood by those skilled in the art that the foregoing and various other changes, omissions and additions may be made therein and thereto, without departing from the spirit and scope of the present invention. Therefore, the present invention should not be understood as limited to the specific embodiment set out above but to include all possible embodiments which can be embodied within a scope encompassed and equivalents thereof with respect to the feature set out in the appended claims.

What is claimed is:

1. An atomic coordinates generating method generating an atomic coordinate position within a rectangular parallelepiped as an outer frame of a simulated crystal having a predetermined plane orientation, comprising:
   (1) step of deriving a sphere circumscribing said rectangular parallelepiped;
   (2) step of deriving a cubic circumscribing said sphere;
   (3) step of generating atomic coordinates within said cubic;
   (4) step of providing rotation for the generated atomic coordinates for matching a bottom of said cubic with said plane orientation; and
   (5) step of checking whether the atomic coordinates after rotation are present within a rectangular parallelepiped having said predetermined plane orientation, and selecting only coordinates present within said rectangular parallelepiped.

2. An atomic coordinates generating method as set forth in claim 1, wherein said atomic coordinates generating step comprises:
   (a) step of deriving a repetition number of a unit cell in each crystal axis direction; and
   (b) step of generating the atomic position coordinates on the basis of said repetition number and an atom position within a unit cell.

3. An atomic coordinates generating method as set forth in claim 1, wherein said atomic coordinates generating step comprises:
   (a) step of deriving a repetition number of a unit cell in each crystal axis direction; and
   (b) step of generating the atomic position coordinates on the basis of said repetition number and an atom position within a unit cell,
   steps from (b) to (5) are repeated for all atomic coordinates within said cubic.

4. An atomic coordinates generating method as set forth in claim 1, wherein respective edges of said cubic are parallel to x, y and z axes of orthogonal coordinates and (001) plane of crystal included in said rectangular parallelepiped is parallel to an x-y plane of said orthogonal coordinates.

5. An atomic coordinates generating method as set forth in claim 1, wherein respective edges of said cubic are parallel to x, y and z axes of orthogonal coordinates and (001) plane of crystal included in said rectangular parallelepiped is parallel to an x-y plane of said orthogonal coordinates,
   in advance of said step (4), a rotational transformation matrix being obtained beforehand for placing said plane orientation in parallel with said x-y plane.

6. An atomic coordinates generating system generating an atomic coordinate position within a rectangular parallelepiped as an outer frame of a simulated crystal having a predetermined plane orientation, comprising:
   means for inputting a crystal size, a lattice constant, a relative atom position in a unit cell and a Miller index as parameters;
   position generating and region calculating means for deriving a sphere circumscribing said rectangular parallelepiped from said crystal size, deriving a size of a cubic circumscribing said sphere, and deriving a repetition number of unit cell on the basis of the size of said cubic and said lattice constant, as a position generating region;

atomic position generating means for generating the unit cell within said position generating region and generating atom coordinates according to said relative atom position in the unit cell;

rotational transformation means for providing rotation for matching a bottom of said cubic with said plane orientation with respect to derived atomic coordinates; and region judgment means for checking whether the atom coordinates after rotation are present within the rectangular parallelepiped having said predetermined plane orientation and selecting only atom coordinates presenting within said rectangular parallelepiped.

7. An atomic coordinates generating system as set forth in claim 6, wherein respective edges of said cubic are parallel to x, y and z axes of orthogonal coordinates and (001) plane of crystal included in said rectangular parallelepiped is parallel to an x-y plane of said orthogonal coordinates, said system further comprises means for preliminarily obtaining a rotational transformation matrix for placing said plane orientation in parallel with said x-y plane in advance of process by said rotational transformation means.

8. An atomic coordinates generating system as set forth in claim 6, wherein a process of generation of atomic coordinates by said atomic position generating means to selection by said region judgment means is repeated for all atomic coordinates within said cubic.

9. A computer readable memory storing an atomic coordinates generating program generating an atomic coordinates position within a rectangular parallelepiped as an outer frame of a crystal having a predetermined plane orientation, as loaded and executed by a computer, said atomic coordinates generating program comprising:

(1) step of deriving a sphere circumscribing said rectangular parallelepiped;

(2) step of deriving a cubic circumscribing said sphere;

(3) step of generating atomic coordinates within said cubic;

(4) step of providing rotation for the generated atomic coordinates for matching a bottom of said cubic with said plane orientation; and (5) step of checking whether the atomic coordinates after rotation are present within a rectangular parallelepiped having said predetermined plane orientation, and selecting only coordinates present within said rectangular parallelepiped.

10. A computer readable memory as set forth in claim 9, wherein said atomic coordinates generating step comprises:

(a) step of deriving a repetition number of a unit cell in each crystal axis direction; and (b) step of generating the atomic position coordinates on the basis of said repetition number and an atom position within a unit cell.

11. A computer readable memory as set forth in claim 9, wherein said atomic coordinates generating step comprises:

(a) step of deriving a repetition number of a unit cell in each crystal axis direction; and (b) step of generating the atomic position coordinates on the basis of said repetition number and an atom position within a unit cell, steps from (b) to (5) are repeated for all atomic coordinates within said cubic.

12. A computer readable memory as set forth in claim 9, wherein respective edges of said cubic are parallel to the x, y and z axes of the orthogonal coordinates and the (001) plane of the crystal included in said rectangular parallelepiped is parallel to an x-y plane of said orthogonal coordinates.

13. A computer readable memory as set forth in claim 9, wherein respective edges of said cubic are parallel to the x, y and z axes of the orthogonal coordinates and the (001) plane of the crystal included in said rectangular parallelepiped is parallel to an x-y plane of said orthogonal coordinates, in advance of said step (4), a rotational transformation matrix being obtained for placing said plane orientation in parallel with said x-y plane.

* * * * *